United States Patent
Komine et al.

(10) Patent No.: US 8,934,004 B2
(45) Date of Patent: Jan. 13, 2015

(54) ENDOSCOPE SYSTEM

(71) Applicant: Olympus Medical Systems Corp., Tokyo (JP)

(72) Inventors: Hitoshi Komine, Hachioji (JP); Takehide Fujimoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/872,218

(22) Filed: Apr. 29, 2013

(65) Prior Publication Data

US 2013/0271586 A1  Oct. 17, 2013

Related U.S. Application Data

(63) Continuation of application No. PCT/JP2012/080711, filed on Nov. 28, 2012.

(30) Foreign Application Priority Data

Dec. 15, 2011 (JP) .................. 2011-274948

(51) Int. Cl.
| | |
|---|---|
| H04N 9/47 | (2006.01) |
| H04N 7/18 | (2006.01) |
| A62B 1/04 | (2006.01) |
| A61B 1/04 | (2006.01) |

(Continued)

(52) U.S. Cl.
CPC ........ *A61B 1/00009* (2013.01); *A61B 1/00006* (2013.01); *A61B 1/045* (2013.01); *G02B 23/2484* (2013.01); *H04N 5/23203* (2013.01); *H04N 2005/2255* (2013.01); *H04N 5/04* (2013.01); *H04N 5/3765* (2013.01)

USPC .............................................. 348/65; 348/74

(58) Field of Classification Search
None
See application file for complete search history.

(56) References Cited

U.S. PATENT DOCUMENTS 5,585,840 A * 12/1996 Watanabe et al. ............... 348/65
7,355,625 B1 * 4/2008 Mochida et al. ............... 348/65

(Continued)

FOREIGN PATENT DOCUMENTS

| EP | 1 798 962 A2 | 6/2007 |
|---|---|---|
| JP | 11-161236 A | 6/1999 |
| JP | 2007-159991 A | 6/2007 |

*Primary Examiner* — Joseph Ustaris
*Assistant Examiner* — Kevin McInnish
(74) *Attorney, Agent, or Firm* — Scully, Scott, Murphy & Presser, P.C.

(57) ABSTRACT

An endoscope system includes an endoscope including a CCD for generating an image pickup signal, and a processor including a video processing circuit. The processor includes: a VCXO that generates a reference clock signal; a PLL circuit that synchronizes a phase of the image pickup signal to be inputted and a phase of the reference clock signal; a synchronization detection circuit that detects whether the phase of the image pickup signal synchronizes with the phase of the reference clock signal; and a multiplexer that controls the video processing circuit, on the basis of the detection result by the synchronization detection circuit, to cause the video processing circuit to output a predetermined video when a non-phase-synchronized state is detected, and to cause the video processing circuit to output a video signal obtained by processing the image pickup signal by the video processing circuit when a phase-synchronized state is detected.

1 Claim, 5 Drawing Sheets

(51) Int. Cl.
*A61B 1/00* (2006.01)
*A61B 1/045* (2006.01)
*G02B 23/24* (2006.01)
*H04N 5/232* (2006.01)
*H04N 5/225* (2006.01)
*H04N 5/04* (2006.01)
*H04N 5/376* (2011.01)

(56) References Cited

U.S. PATENT DOCUMENTS

2002/0145661 A1\* 10/2002 Takahashi et al. ............... 348/65
2007/0139521 A1\* 6/2007 Takahashi ....................... 348/65

\* cited by examiner

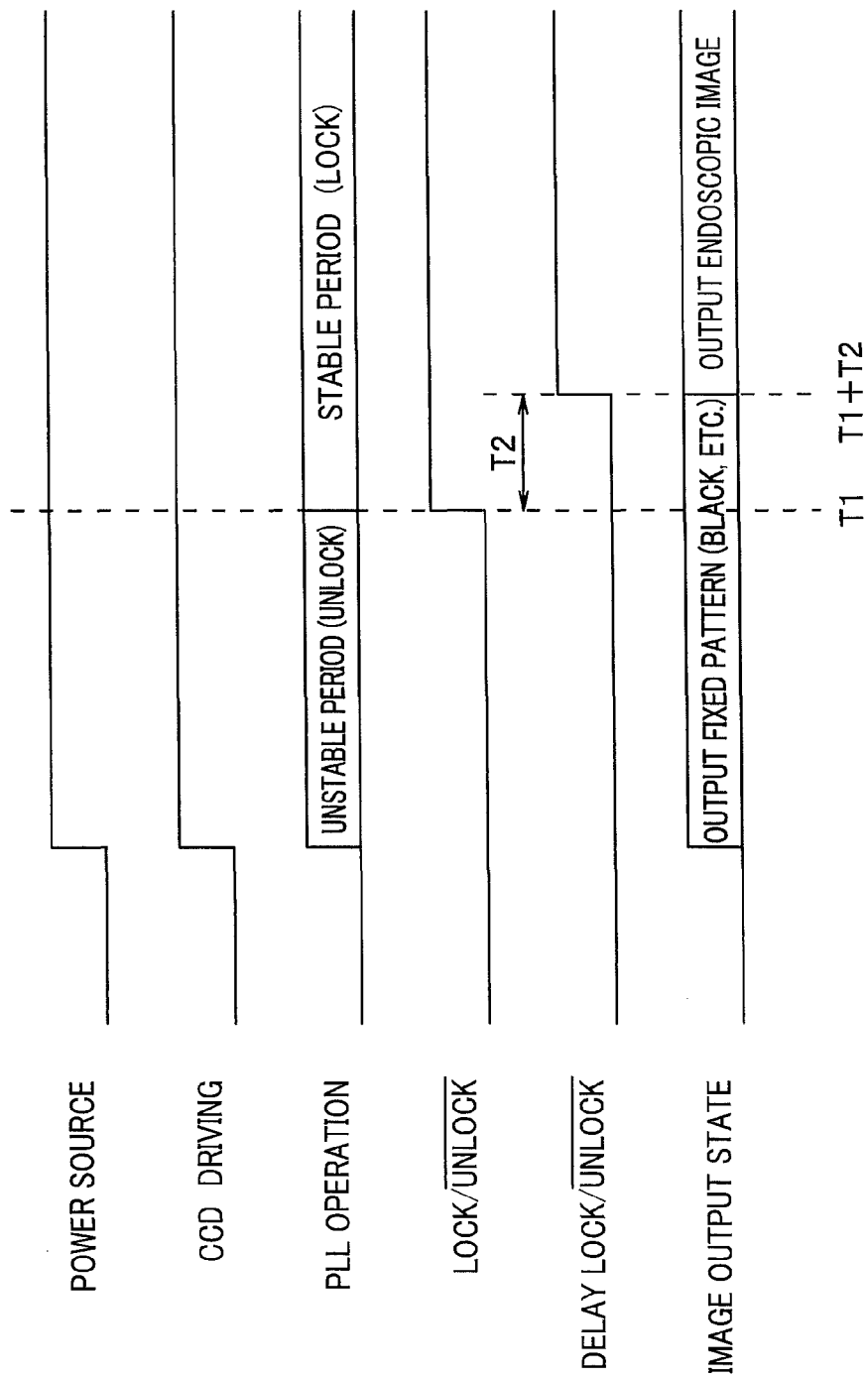

ENDOSCOPE SYSTEM

CROSS REFERENCE TO RELATED APPLICATION

This application is a continuation application of PCT/JP2012/080711 filed on Nov. 28, 2012 and claims benefit of Japanese Application No. 2011-274948 filed in Japan on Dec. 15, 2011, the entire contents of which are incorporated herein by this reference.

BACKGROUND OF THE INVENTION

1. Field of the Invention

The present invention relates to an endoscope system and more particularly to an endoscope system that outputs an optimal image according to a synchronized state between a phase an image pickup signal and a phase of a reference clock signal.

2. Description of the Related Art

Conventionally, an endoscope system has been constituted by a scope (endoscope) including an image pickup device such as CCD at a distal end portion, and a processor that performs predetermined image processing on an endoscopic image picked up by the image pickup device provided in the scope and displays the processed endoscopic image on a monitor. The scope and the processor are detachably connected to each other via a connector and the like, and different kinds of scopes can be connected to the processor.

The processor in such an endoscope system is provided with a PLL circuit for synchronizing a phase of an image pickup signal inputted from the endoscope and a phase of a reference clock signal which is a reference of a sampling pulse for sampling the image pickup signal.

For example, Japanese Patent Application Laid-Open Publication No. 2007-159991 discloses an endoscope system provided with a PLL circuit that is capable of performing frequency pull-in with a simple configuration with low-phase-noise characteristics being set, in order to perform signal processing adaptable to an endoscope incorporating a high-pixel image pickup device.

SUMMARY OF THE INVENTION

An endoscope system according to one aspect of the present invention includes: an endoscope including an image pickup device that picks up an image of a subject and generates an image pickup signal; and a processor including a signal processing circuit that performs signal processing on the image pickup signal inputted from the endoscope, the processor including: a clock generation section that generates a reference clock signal as a reference of a sampling pulse for sampling the image pickup signal; a synchronization section that synchronizes a phase of the image pickup signal inputted from the endoscope with a phase of the reference clock signal; a synchronization detection section that detects whether the phase of the image pickup signal and the phase of the reference clock signal are synchronized with each other by the synchronization section; and a control section that controls the signal processing circuit, on the basis of a detection result by the synchronization detection section, to cause the signal processing circuit to output a predetermined video, when it is detected that the phase of the image pickup signal and the phase of the reference clock signal are not synchronized with each other, and to cause the signal processing circuit to output a video signal obtained by processing the image pickup signal by the signal processing circuit, when it is detected that the phase of the image pickup signal and the phase of the reference clock signal are synchronized with each other.

BRIEF DESCRIPTION OF THE DRAWINGS

FIG. 5 is a timing chart for describing an operation of an endoscope system 1b according to the second embodiment.

DETAILED DESCRIPTION OF THE PREFERRED EMBODIMENTS

Hereinafter, embodiments of the present invention will be described with reference to drawings.

First Embodiment

First, a configuration of an endoscope system according to the first embodiment of the present invention will be described with reference to FIG. 1.

Figure 1:
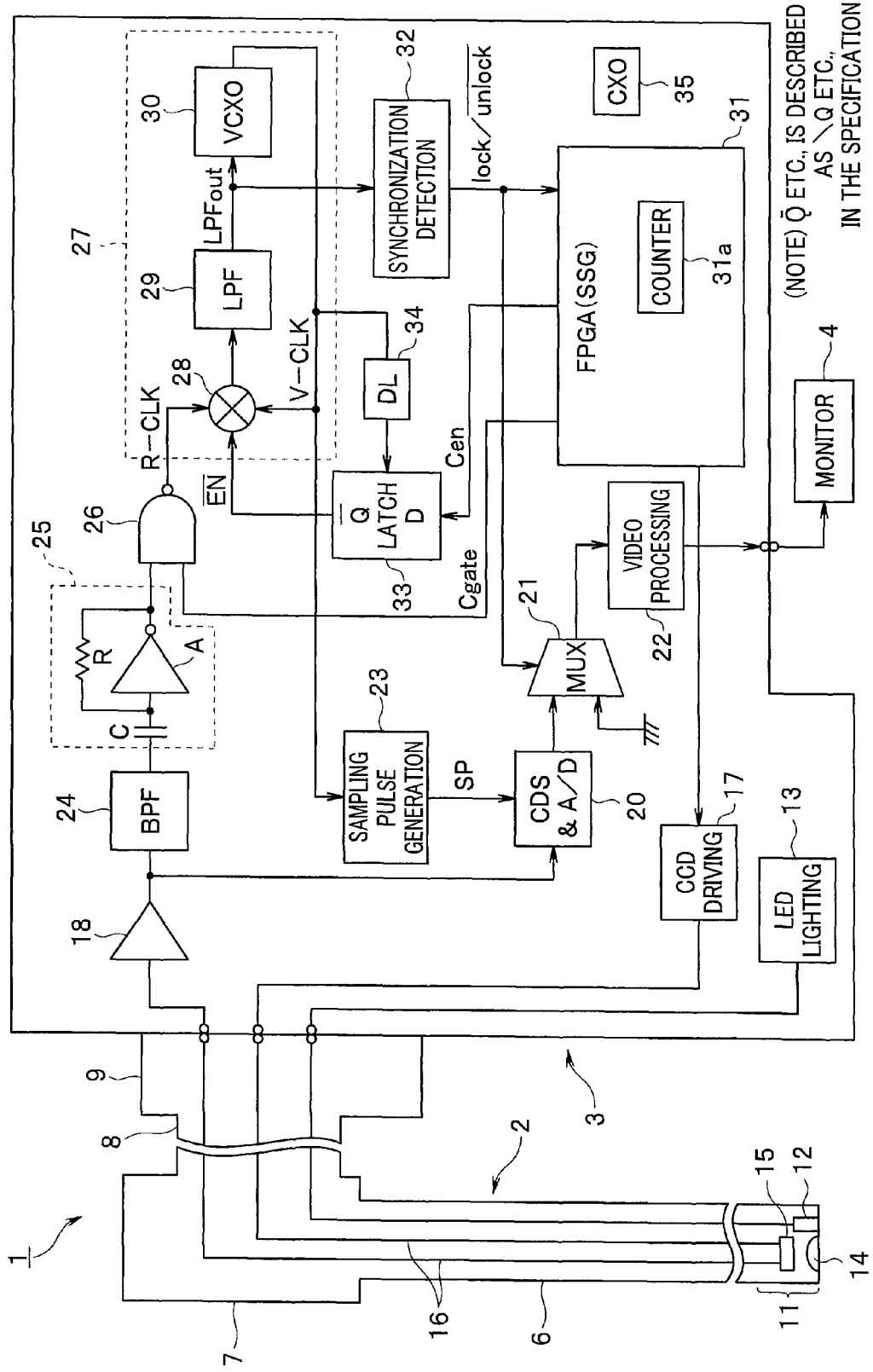
FIG. 1 illustrates a configuration of an endoscope system according to a first embodiment.

FIG. 1 illustrates the configuration of the endoscope system according to the first embodiment.

As shown in FIG. 1, the endoscope system 1 includes: an endoscope 2 for performing endoscopic examination; a processor 3 to which the endoscope 2 is detachably connected, the processor performing signal processing on an image pickup device mounted in the endoscope 2; and a monitor 4 to which a video signal outputted from the processor 3 is inputted and which displays an image picked up by the image pickup device as an endoscopic image.

The endoscope 2 includes an elongated insertion portion 6 configured to be inserted into a body cavity or the like, an operation portion 7 formed at the rear end (proximal end) of the insertion portion 6, and a universal cable portion 8 that is extended from the operation portion 7. A connector 9 provided at the rear end of the universal cable portion 8 is detachably connected to the processor 3.

An illumination window through which illumination light is emitted is provided at a distal end portion 11 provided at a distal end of the insertion portion 6. For example, a white LED 12 is attached to the illumination window, and power source for lighting the LED is supplied from an LED lighting circuit 13 provided at the processor 3 to the white LED 12, via a drive wire. The white LED 12 is thereby lit to emit white illumination light.

An objective lens 14 is attached to an observation window (image pickup window) provided adjacent to the illumination window, and a charge coupled device (abbreviated as CCD) 15, for example, is arranged as an image pickup device at an image-forming position of the objective lens 14.

The CCD 15 is connected to a CCD driving circuit 17 provided in the processor 3 and a front-end amplifier (abbreviated as FEA) 18 provided in the processor 3, via a signal cable 16 inserted through the interior of the insertion portion 6 and other portions.

A CCD driving signal outputted in a certain cycle from the CCD driving circuit 17 and including a reset pulse $\phi R$ and the like is applied to the CCD 15 via a drive wire of the signal cable 16, thereby causing the CCD 15 to perform photoelectric conversion and output a signal charge accumulated by photoelectric conversion, as an image pickup signal (or CCD output signal). The image pickup signal is inputted to the FEA 18 via a signal line of the signal cable 16. The FEA 18 amplifies the inputted image pickup signal and outputs the amplified image pickup signal to a correlative double sampling & analog-to-digital (CDS & A/D) circuit 20 and a band-pass filter (BPF) 24.

Note that, in FIG. 1, the CCD 15 is a high-pixel CCD having a number of pixels about three times as large as the usual number of pixels of a normal CCD. Therefore, in contrast with the frequency (about 10 MHZ) of a horizontal transfer pulse and a reset pulse φR in the case of usual number of pixels, the frequency of horizontal transfer pulse and reset pulse φR is set to a high frequency of about 30 MHZ in the present embodiment. In addition, though one endoscope 2 is shown in FIG. 1, the signal processing system is formed by using a phase-locked loop (PLL) circuit 27 so that the processor 3 shown in FIG. 1 can be adapted in common with endoscopes having different cable lengths including the length of the insertion portion 6.

The image pickup signal amplified by the FEA 18 is inputted to the CDS & A/D circuit 20, and a signal portion of the image pickup signal is extracted and converted into a baseband signal by correlated double sampling (CDS) processing in the CDS circuit part, and thereafter converted into a digital signal in the A/D circuit part.

The digital signal is inputted to one input terminal of a multiplexer (abbreviated as MUX in FIG. 1) 21. In addition, the other input terminal of the multiplexer 21 is connected to GND, and dummy data (all zero in this case) is inputted to the other input terminal. In addition, a detection signal from a synchronization detection circuit 32 to be described later is inputted into the multiplexer 21, as a selection signal. The detection signal indicates whether or not the PLL circuit 27 is in a phase-synchronized state. For example, when the PLL circuit 27 is in the phase-synchronized state or in a frequency pull-in state (lock), the detection signal becomes "H" level, and when the PLL circuit 27 is in a non-pull-in state (\unlock), i.e., a state of phase-synchronization failure, the detection signal becomes "L" level.

The multiplexer 21 selects the output from the CDS & A/D circuit 20 or the output of dummy data (dummy signal) on the basis of the detection signal from the synchronization detection circuit 32 and outputs the selected one to the video processing circuit 22. Specifically, when the detection signal is "H" level, that is, when the PLL circuit 27 is in the phase-synchronized state, or in the frequency pull-in state (lock), the multiplexer 21 selects the output from the CDS & A/D circuit 20, and when the detection signal is "L" level, that is, when the PLL circuit 27 is in the non-pull-in state (\unlock) i.e., the state of phase synchronization failure, the multiplexer 21 selects the dummy data. The multiplexer 21 constitutes a control section that controls the video processing circuit 22 to be described later, on the basis of the detection signal from the synchronization detection circuit 32, to cause the video processing circuit to output a predetermined video.

When the digital signal from the CDS & A/D circuit 20 is selected in the multiplexer 21, the video processing circuit 22 converts the digital signal into a video signal and outputs an endoscopic image to the monitor 4. On the other hand, when the output of the dummy data is selected in the multiplexer 21, the video processing circuit 22 outputs a predetermined video, for example, a black image to the monitor 4. Note that the predetermined video is not limited to a black image but may be a color bar or text information, for example.

To the above-described CDS circuit part, a sampling pulse SP synchronized with a variable clock V-CLK outputted from the PLL circuit 27, to be described later, is supplied from a sampling pulse generation circuit 23.

The CDS circuit part samples the signal portion of the image pickup signal using the sampling pulse SP. By using the sampling pulse, a field-through portion (immediately after the reset pulse) and a luminance information portion in the image pickup signal are respectively sampled, and a signal representing the difference therebetween is extracted, thereby generating the baseband signal.

The image pickup signal amplified by the FLA 18 is passed through the band-pass filter (BPF) 24 which is band-restricted such that the reset pulse φR in a phase adjustment period is extracted (as a reference clock), and is further subjected to waveform shaping in a limiter amplifier 25.

The limiter amplifier 25 is constituted by, for example, an inverting amplifier A. A capacitor C for passage of an alternating current signal and a resistor R are connected between input and output terminals of the inverting amplifier A.

The reset pulse φR signal subjected to the waveform shaping in the limiter amplifier 25 is inputted as a reference clock R-CLK to a phase comparator 28 constituting the PLL circuit 27, via a reference clock gate (hereinafter shortly referred to as R-gate) 26. The R-gate 26 is constituted by a NAND circuit, for example. Note that the R-gate 26 forms gate means that opens and closes a path for input of the reference clock R-CLK to the PLL circuit 27.

When an intermittent operation control signal \EN to be described later is applied at "L" level to the phrase comparator 28, the phase comparator 28 performs a phase comparison operation. When the intermittent operation control signal \EN becomes "H" level, the phase comparator 28 stops the phase comparison operation.

The phase comparator 28 compares the phase of the reference clock R-CLK inputted thereto via the R-gate 26 and the phase of the variable clock V-CLK outputted from a voltage-controlled oscillator (VCXO) 30, and outputs a signal corresponding to the phase difference therebetween to a low-pass filter (LPF) 29.

The LPG 29 outputs to the VCXO 30 a signal formed of a low-frequency component of the output signal from the phase comparator 28, as an output signal LPFout from the LPF 29. Then, the VCXO 30 outputs the variable clock V-CLK, the oscillation frequency of which varies, according to (for example, substantially in proportional to) the voltage value of the output signal LPFout from the LPF 29 which is applied to the input terminal of the VCXO 30.

That is, the VCXO 30 outputs to the phase comparator 28 the variable clock V-CLK, the frequency or the phase of which corresponds to the voltage value of the output signal LPFout from the LPF 29 and the VCXO 30 also outputs the variable clock V-CLK to the sampling pulse generation circuit 23. The variable clock V-CLK is a reference clock signal which is a reference of the sampling pulse SP for sampling the image pickup signal, and the sampling pulse generation circuit 23 generates the sampling pulse SP synchronized with the variable clock V-CLK. Thus, the VCXO 30 constitutes a clock generation section that generates the reference clock signal as a reference of the sampling pulse SP for sampling the image pickup signal.

In the present embodiment, the PLL circuit 27 is a circuit for generating the sampling pulse SP at an appropriate timing without any adjustment, even when a cable having a different length is used. Since the frequency of the reference clock R-CLK is almost constant (determined depending on the number of pixels of the CCD 15), in accordance with the almost constant frequency, a crystal oscillation device having high frequency stability is used in the VCXO 30 to generate the variable clock V-CLK.

That is, in the present embodiment, in order to synchronize the phase of the variable clock V-CLK with the phase of the reference clock R-CLK, the PLL circuit 27 constituting a synchronization section is used (the frequency of the reference clock R-CLK and the frequency of the variable clock can therefore be considered to be substantially equal to each other, even if the width of variation in which the frequency of the variable clock V-CLK is changed is taken into consideration).

Note that, in the present embodiment, the phase comparator 28 detects a timing discrepancy between the rising edge of the variable clock V-CLK and the rising edge of the reference clock R-CLK, i.e., the output timing phase difference between the two clocks. Then, the phase comparator 28 outputs a signal corresponding to the phase difference to the LPF 29.

For example, if the timing of the rising edge of the variable clock V-CLK is in advance of the timing of the rising edge of the reference clock R-CLK, the voltage value of the output signal LPFout from the LPF 29 decreases in correspondence with the phase difference and the oscillation frequency of the variable clock V-CLK from the VCXO 30 is reduced so as to delay the timing of the rising edge of the variable clock V-CLK (the phase of the variable clock V-CLK is delayed to reduce the phase difference).

In a case opposite to the above, the oscillation frequency of the variable clock V-CLK from the VCXO 30 is increased (the phase of the variable clock V-CLK is advanced so as to reduce the phase difference).

In addition, the higher the voltage value of the output signal LPFout from the LPF 29 is, for example, the more the frequency of the variable clock V-CLK is increased (that is, the phase is advanced).

Furthermore, the R-gate 26 performs opening/closing control on the operation to input the reference clock R-CLK to the phase comparator 28 according to an R-gate opening/closing control signal Cgate from a field programmable gate array (FPGA) 31 constituting the reference signal generation circuit (SSG).

That is, in the present embodiment, it is possible to switch between the state where the reference clock R-CLK is inputted to the phase comparator 28 of the PLL circuit 27 and the state where the reference clock R-CLK is not inputted to the phase comparator 28 of the PLL circuit 27, to thereby enable the frequency pull-in operation to be smoothly and rapidly performed by the PLL circuit 27.

Thus, it is ensured that frequency pull-in can be performed with stability when the frequency pull-in operation is first started, and that even in a case where the frequency pull-in ends in failure, or pull-in is cancelled, the frequency pull-in operation can be again performed in a suitable state by the PLL circuit 27 by closing the R-gate 26 and thereafter by opening the R-gate 26.

Note that the R-gate opening/closing control signal Cgate is set to an open state or closed state (on/off), for example, in a period other than the phase adjustment period. For example, during some phase adjustment periods, the R-gate opening/closing control signal Cgate is set to the closed state (that is, the reference clock R-CLK to the phase comparator 28 is shut off) and the PLL circuit 27 is set in such a state that the output signal LPFout from the LPF 29 sticks to the ground side. In this state, when the R-gate opening/closing control signal Cgate is set to the open state (the reference clock R-CLK is inputted to the phase comparator 28) (as described later), the frequency pull-in operation is substantially started.

The output signal LPFout from the LPF 29 is inputted to the synchronization detection circuit (or pull-in detection circuit) 32. The synchronization detection circuit 32 as a synchronization detection section detects, from the level of the output signal LPFout, that the PLL circuit 27 is in the phase-synchronized state or in the frequency pull-in state (lock), or in the non-pull-in state (\unlock) i.e., the state of phase synchronization failure, and outputs a detection signal to the multiplexer 21 and the FPGA 31. As described above, when the PLL circuit 27 is in the phase-synchronized state or the frequency pull-in state (lock), the synchronization detection circuit 32 outputs an "H" level signal as the detection signal. When the PLL circuit 27 is in the non-pull-in state (\unlock) i.e., the state of phase synchronization failure, the synchronization detection circuit 32 outputs an "L" level signal as the detection signal.

The FPGA 31 inputs the detection signal from the synchronization detection circuit 32 to a counter circuit 31a which is provided in the FPGA 31, for example, counts the clock of an oscillator 35, and monitors the time period during which the phase-synchronized state is maintained.

If the non-phase-synchronized state continues beyond a predetermined time period tc, on the basis of the output from the counter circuit 31a, the FPGA 31 performs control operation to close the R-gate 26 by setting the R-gate opening/closing control signal Cgate to the closed (off) state and thereafter to open the R-gate 26 by setting the R-gate opening/closing control signal Cgate to open (on) state, to enable the reference clock R-CLK to be inputted to the phase comparator 28 of the PLL circuit 27.

Thus, it is possible to perform the frequency pull-in operation again by the PLL circuit 27. In addition, also in an initial state after the turning-on of the power source, the FPGA 31 performs the control operation to turn off the R-gate opening/closing control signal Cgate and thereafter turn on the R-gate opening/closing control signal Cgate. Then, the FPGA 31 performs the frequency pull-in operation using the process by which the frequency pull-in can be easily performed.

In addition, on the basis of the detection signal from the synchronization detection circuit 32, the FPGA 31 monitors whether or not the PLL circuit 27 is in the synchronization state, and if the non-phase-synchronized state continues beyond the predetermined time period tc, the FPGA 31 restarts the frequency pull-in operation again.

In addition, in the present embodiment, a timing is set to ensure that the frequency pull-in operation can be appropriately performed when the frequency pull-in operation is started by the PLL circuit 27 in the phase adjustment period.

To this end, the FPGA 31 outputs a control signal Cen to a latch circuit 33, whereby the intermittent operation control signal \EN is applied to the phase comparator 28 as an operation control signal for starting the frequency pull-in operation by the PLL circuit 27. The control signal Cen is outputted so as to cover an intermittent phase adjustment period.

The control signal Cen is applied to a D input terminal of the latch circuit 33, and the variable clock V-CLK from the VCXO 30 is delayed by a predetermined delay time period Ta by a delay circuit (abbreviated as DL in FIG. 1) 34, to be applied to a clock input terminal of the latch circuit 33.

In the phase adjustment period, the control signal Cen becomes "H" level and the intermittent operation control signal \EN is applied from a \Q output terminal of the latch circuit 33 to the phase comparator 28 at the timing delayed by the delay circuit 34 by the delay time period Ta from the timing of the rising edge of the variable clock V-CLK outputted first from the VCXO 30 after the timing at which the control signal Cen becomes "H" level.

That is, when the PLL circuit 27 intermittently starts the frequency pull-in operation by the control of the phase comparison operation by the phase comparator 28, the timing at which the intermittent operation control signal \EN is applied to the phase comparator 28 is set by the delay circuit 34 and the latch circuit 33. The timing is set so that the intermittent operation control signal \EN is synchronized with the timing of the rising edge of the variable clock V-CLK within the predetermined time period.

Note that the FPGA 31 generates the above-described control signal using the reference clock generated by the oscillator 35 formed by the crystal oscillation device having high oscillation frequency stability, and supplies the CCD driving circuit 17 with a timing signal as a reference at the time of generating the CCD driving signal.

Next, the operation of the endoscope system 1 thus configured will be described.

Figure 2:
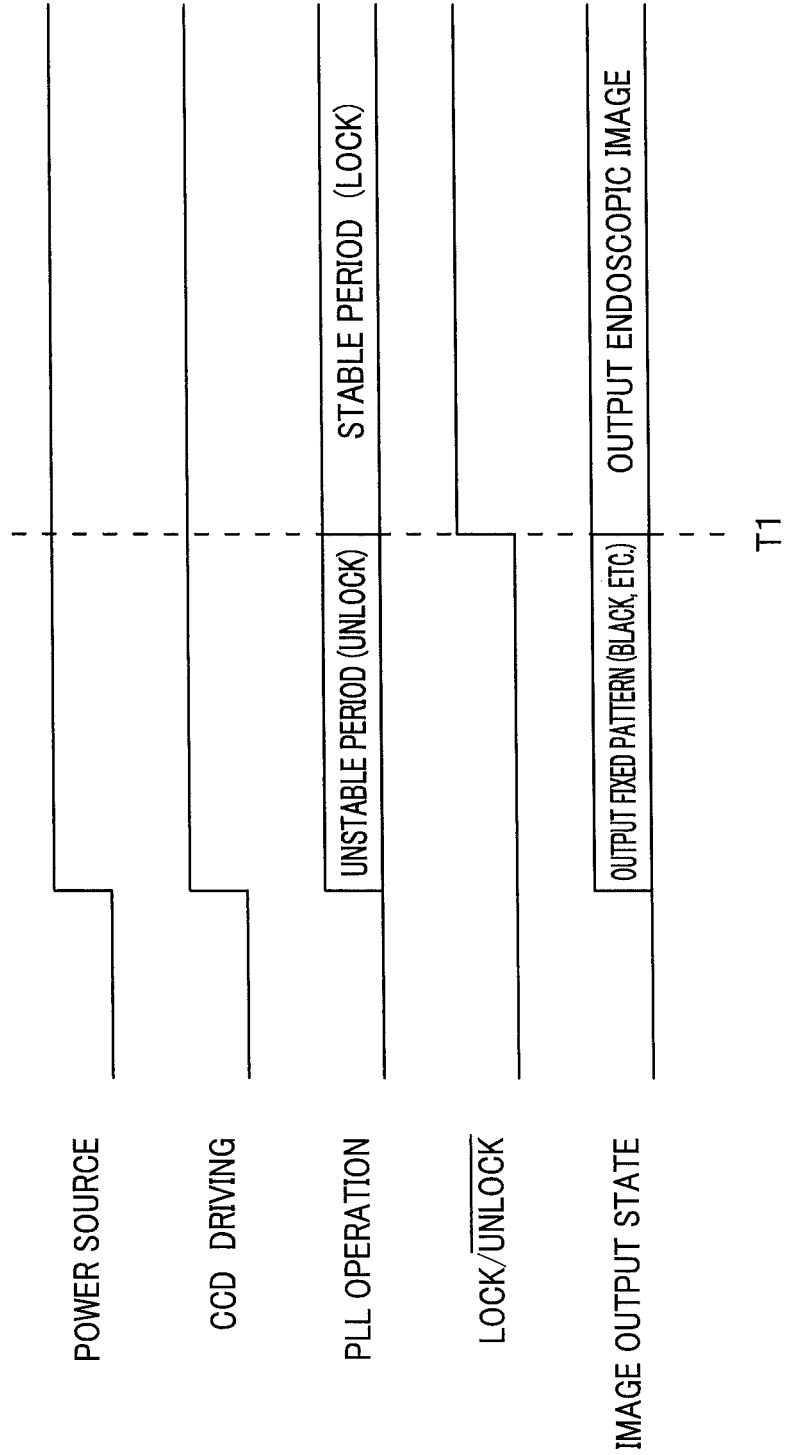
FIG. 2 is a timing chart for describing an operation of the endoscope system 1 according to the first embodiment.

FIG. 2 is a timing chart for describing the operation of the endoscope system 1 according to the first embodiment.

As shown in FIG. 1, when performing endoscopic examination, the person who performs examination uses the endoscope 2 including the insertion portion having a length suitable for the endoscopic examination, and connects the endoscope 2 to the processor 3. Then, the person who performs examination turns on the power source, not shown, of the processor 3. When the power source is turned on, the FPGA 31 of the processor 3 is brought into an activated state, to supply a timing signal to the CCD driving circuit 17.

The CCD driving circuit 17 generates a CCD driving signal on the basis of the timing signal, to supply the generated CCD driving signal to the CCD 15. When receiving the CCD driving signal, the CCD 15 performs photoelectric conversion and outputs a signal charge accumulated by photoelectric conversion, as an image pickup signal.

The synchronization detection circuit 32 outputs a \unlock signal of "L" level as the detection signal in an unstable period (unlock) in which the phase of the image pickup signal and the phase of the reference clock signal (variable clock signal) V-CLK are not synchronized with each other. The detection signal is supplied to the multiplexer 21. When receiving the \unlock signal of "L" level as the detection signal, the multiplexer 21 selects dummy data (all zero), to output the dummy data to the video processing circuit 22. When receiving the dummy data, the video processing circuit 22 outputs a predetermined video (for example, a fixed pattern such as a black image, etc.) to the monitor 4.

When a stable period (lock) in which the phase of the image pickup signal and the phase of the reference clock signal are synchronized with each other starts at time T1, the synchronization detection circuit 32 outputs a lock signal of "H" level as the detection signal. The detection signal is supplied to the multiplexer 21. When receiving the lock signal of "H" level as the detection signal, the multiplexer 21 selects the image pickup signal from the CDS & A/D circuit 20, to output the image pickup signal to the video processing circuit 22. When receiving the image pickup signal, the video processing circuit 22 outputs an endoscopic image obtained by performing video processing on the image pickup signal to the monitor 4.

Note that, in the timing chart in FIG. 2, the operation at the time of turning on the power source is described. However, even when an out-of-synchronization state occurs due to disturbance or the like during the use of the endoscope 2, a predetermined video such as a black image is displayed on the monitor 4 in the same manner as when the power source is turned on. Furthermore, when the out-of-synchronization state occurs due to disturbance or the like during the use of the endoscope 2, an endoscopic image (freeze image) picked up immediately before the image is disturbed due to the occurrence of the out-of-synchronization state may continue to be displayed on the monitor 4 until the synchronization state is established.

As described above, the processor 3 in the endoscope system 1 is provided with the multiplexer 21 that switches between the output of the image pickup signal from the CDS & A/D circuit 20 and the output of the dummy data (all zero), on the basis of the detection signal (lock signal or \unlock signal) from the synchronization detection circuit 32. When receiving the lock signal, the multiplexer 21 outputs the image pickup signal from the CDS & A/D circuit 20 to the video processing circuit 22, and when receiving the \unlock signal, the multiplexer 21 outputs the dummy data to the video processing circuit 22.

When receiving the image pickup signal from the CDS & A/D circuit 20, the video processing circuit 22 outputs an endoscopic image to the monitor 4, and when receiving the dummy data, the video processing circuit 22 outputs a predetermined video (for example, black image) to the monitor 4. Thus, an image in the state where the phase of the image pickup signal and the phase of the reference clock signal are not synchronized with each other after the turning-on of the power source is not displayed on the monitor 4.

Therefore, according to the endoscope system of the present embodiment, it is possible to perform control such that the video in a period during which the PLL circuit is not in the synchronization state is not outputted.

Note that, in the present embodiment, the detection signal from the synchronization detection circuit 32 is inputted to the multiplexer 21, and the multiplexer 21 switches between the output of the image pickup signal and the output of the dummy data, thereby switching the image to be outputted to the monitor 4 between the black image and the endoscopic image. However, the present invention is not limited to such a configuration. For example, the detection signal from the synchronization detection circuit 32 may be inputted to the CDS & A/D circuit 20 or the video processing circuit 22, to switch the image to be outputted to the monitor 4 between the black image and the endoscopic image.

First, description will be made on the case where the detection signal from the synchronization detection circuit 32 is inputted to the CDS & A/D circuit 20.

In the case where the detection signal from the synchronization detection circuit 32 is inputted to the CDS & A/D circuit 20, in the period during which the \unlock signal of "L" level is inputted as the detection signal, the CDS & A/D circuit 20 outputs the dummy data (all zero) to the video processing circuit 22. In the period during which the lock signal of "H" level is inputted as the detection signal, the CDS & A/D circuit 20 outputs the image pickup signal to the video processing circuit 22. When receiving the dummy data, the video processing circuit 22 outputs the predetermined image (for example, a fixed pattern such as black image, etc.) to the monitor 4, and when receiving the image pickup signal, the video processing circuit 22 outputs the endoscopic image to the monitor 4.

Next, description will be made on the case where the detection signal from the synchronization detection circuit 32 is inputted to the video processing circuit 22.

In the case where the detection signal from the synchronization detection circuit 32 is inputted to the video processing circuit 22, in a period during which the \unlock signal of "L" level is inputted as the detection signal, the video processing circuit 22 does not perform processing on the image pickup signal from the CDS & A/D circuit 20 but outputs a predetermined video (for example, the fixed pattern such as black image) to the monitor 4. On the other hand, in the period during which the lock signal of "H" level is inputted as the detection signal, the video processing circuit 22 performs video processing on the image pickup signal from the CDS & A/D circuit 20 to output the endoscopic image to the monitor 4.

As described above, if the detection signal from the synchronization detection circuit 32 is inputted to the CDS & A/D circuit 20 or the video processing circuit 22, to perform above-described processing, there is no need for providing the multiplexer 21, which enables the circuit scale of the processor 3 to be reduced.

Modified Example

Next, a modified example of the first embodiment will be described.

Figure 3:
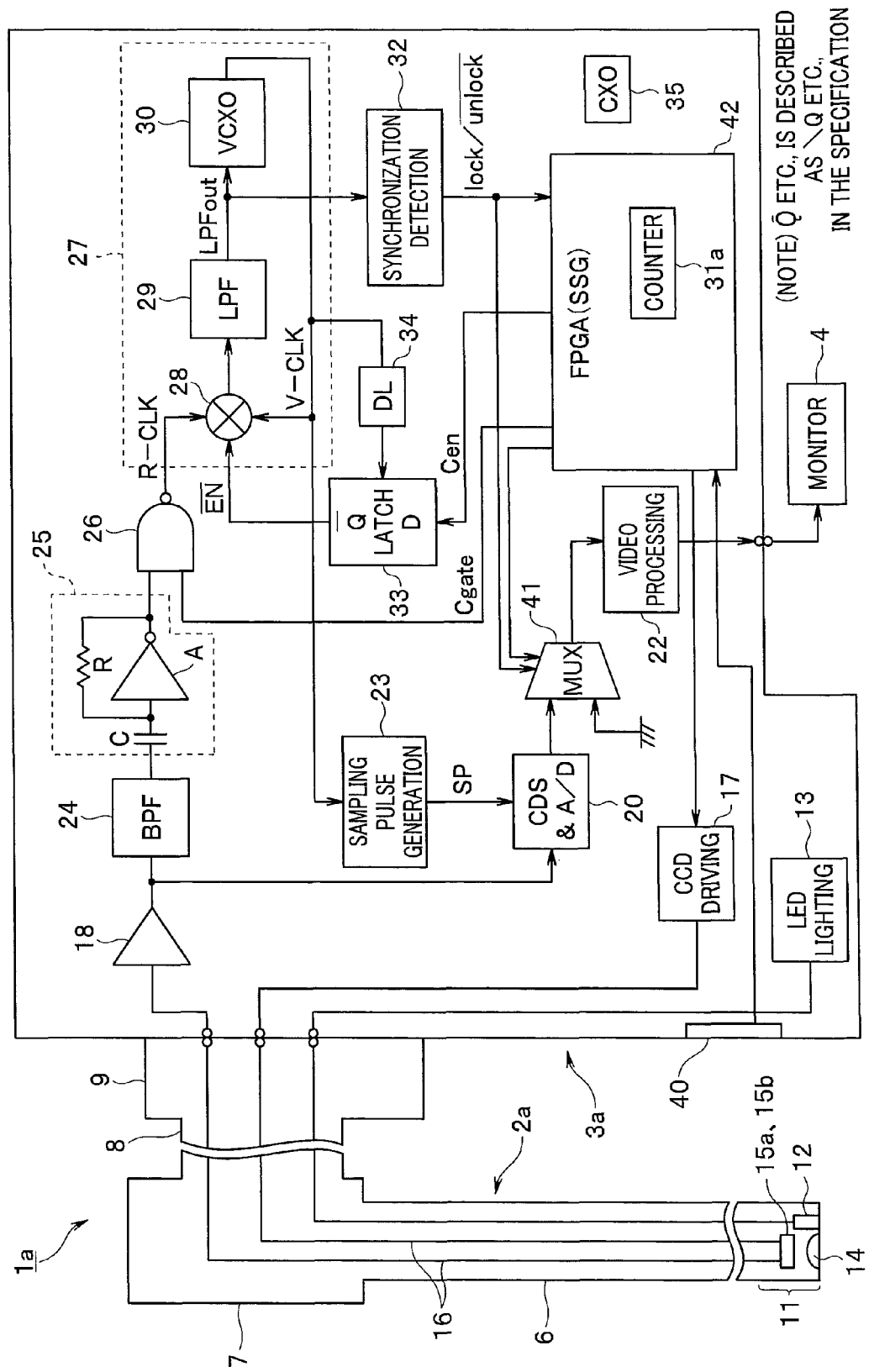
FIG. 3 illustrates a configuration of an endoscope system according to a modified example of the first embodiment.

FIG. 3 illustrates a configuration of an endoscope system according to a modified example of the first embodiment. Note that, in FIG. 3, the same components as those in FIG. 1 are indicated by the same reference numerals and description thereof will be omitted.

As shown in FIG. 3, an endoscope system 1a includes: an endoscope 2a for performing endoscopic examination; a processor 3a to which the endoscope 2a is detachably connected, the processor performing signal processing on the image pickup device mounted in the endoscope 2a; and the monitor 4 to which a video signal outputted from the processor 3 is inputted and which displays an image picked up by the image pickup device as an endoscopic image.

The endoscope 2a is an endoscope to which a plurality of CCDs are mounted. Though illustration is omitted in the present modified example, two CCDs 15a and 15b are mounted.

The processor 3a is provided with a front panel 40 which is used for performing an operation to switch which of the two CCDs 15a and 15b mounted to the endoscope 2a is driven. When the operator operates the front panel 40 to perform operation for switching between the CCDs 15a and 15b, a switching signal is transmitted to the endoscope 2a via a signal line, not shown. According to the operation, for example, switching from the first CCD 15a to the second CCD 15b is performed in the endoscope 2a.

In addition, the processor 3a is configured by using a multiplexer 41 and an FPGA 42 instead of the multiplexer 21 and the FPGA 31 shown in FIG. 1. Then, the switching signal from the front panel 40 is inputted to the FPGA 42.

When receiving the switching signal from the front panel 40, the FPGA 42 outputs a switching control signal of "L" level to the multiplexer 41. The FPGA 42 monitors the switching operation between the CCD 15a and CCD 15b in the endoscope 2a, and when the switching operation between the CCD 15a and the CCD 15b is completed, the FPGA 42 outputs a switching control signal of "H" level to the multiplexer 41. That is, the FPGA 42 outputs the switching control signal of "L" level to the multiplexer 41 in the period during which switching between the CCD 15a and the CCD 15b is performed and observation of the endoscopic image is impossible. In the period during which switching between the CCD 15a and the CCD 15b is completed and observation of the endoscopic image is possible, the FPGA 42 outputs the switching control signal of "H" level to the multiplexer 41.

When receiving the lock signal of "H" level from the synchronization detection circuit 32 and the switching control signal of "H" level from the FPGA 42, the multiplexer 41 selects the output from the CDS & A/D circuit 20 and outputs the signal from the CDS & A/D circuit 20 to the video processing circuit 22. On the other hand, when receiving the \unlock signal of "L" level from the synchronization detection circuit 32 or receiving the switching control signal of "L" level from the FPGA 42, the multiplexer 41 selects the dummy data (all zero) and outputs the dummy data to the video processing circuit 22. That is, the FPGA 42 selects the dummy data (all zero) when either the output from the synchronization detection circuit 32 or the output from the FPGA 42 is "L" level.

Similarly as in the above-described embodiment, when receiving the image pickup signal from the CDS & A/D circuit 20, the video processing circuit 22 outputs the endoscopic image to the monitor 4, and when receiving the dummy data, the video processing circuit 22 outputs a predetermined video (for example, a fixed pattern such as black image) to the monitor 4. Other configurations are the same as those in the above-described embodiment.

Conventionally, when switching between the CCD 15a and the CCD 15b is performed in the endoscope 2a capable of switching between two CCDs, the video processing circuit 22 has performed signal processing on the image pickup signal from the CDS & A/D circuit and displayed on the monitor 4 an image which is not suitable for observation of the endoscopic image also during the switching operation was being performed. In order to prevent the image which is not suitable for the observation from being displayed, it has been possible to display on the monitor 4 the endoscopic image (freeze image) picked up immediately before the switching. However, in such a case, the freeze time period is fixed in the system or can be set by the user. Accordingly, when the freeze time period is short, the image which is not suitable for observation of the endoscopic image is displayed on the monitor 4. On the other hand, when the freeze time period is long, the freeze image continues to be displayed on the monitor 4 even in the state where the switching between the CCD 15a and the CCD 15b is completed and observation of the endoscopic image is possible.

In contrast, according to the endoscope system 1a of the present modified example, when the FPGA 42 detects that the switching operation between the CCD 15a and the CCD 15b is performed on the front panel 40, the FPGA 42 outputs the switching control signal of "L" level to the multiplexer 41 until the switching between the CCD 15a and the CCD 15b is completed. The multiplexer 41 outputs the dummy data to the video processing circuit 22 in the period during which the switching control signal is "L" level, and performs control to cause the video processing circuit 22 to output the predetermined video (for example, the fixed pattern such as black image).

As a result, the endoscope system 1a can stop the output of the endoscopic image in the period during which switching between the CCD 15a and the CCD 15b is performed and which is not suitable for outputting the endoscopic image, and can display the endoscopic image on the monitor 4 at the optimal timing, that is, as soon as the observation of the endoscopic image becomes possible.

Second Embodiment

Next, the second embodiment will be described.

Figure 4:
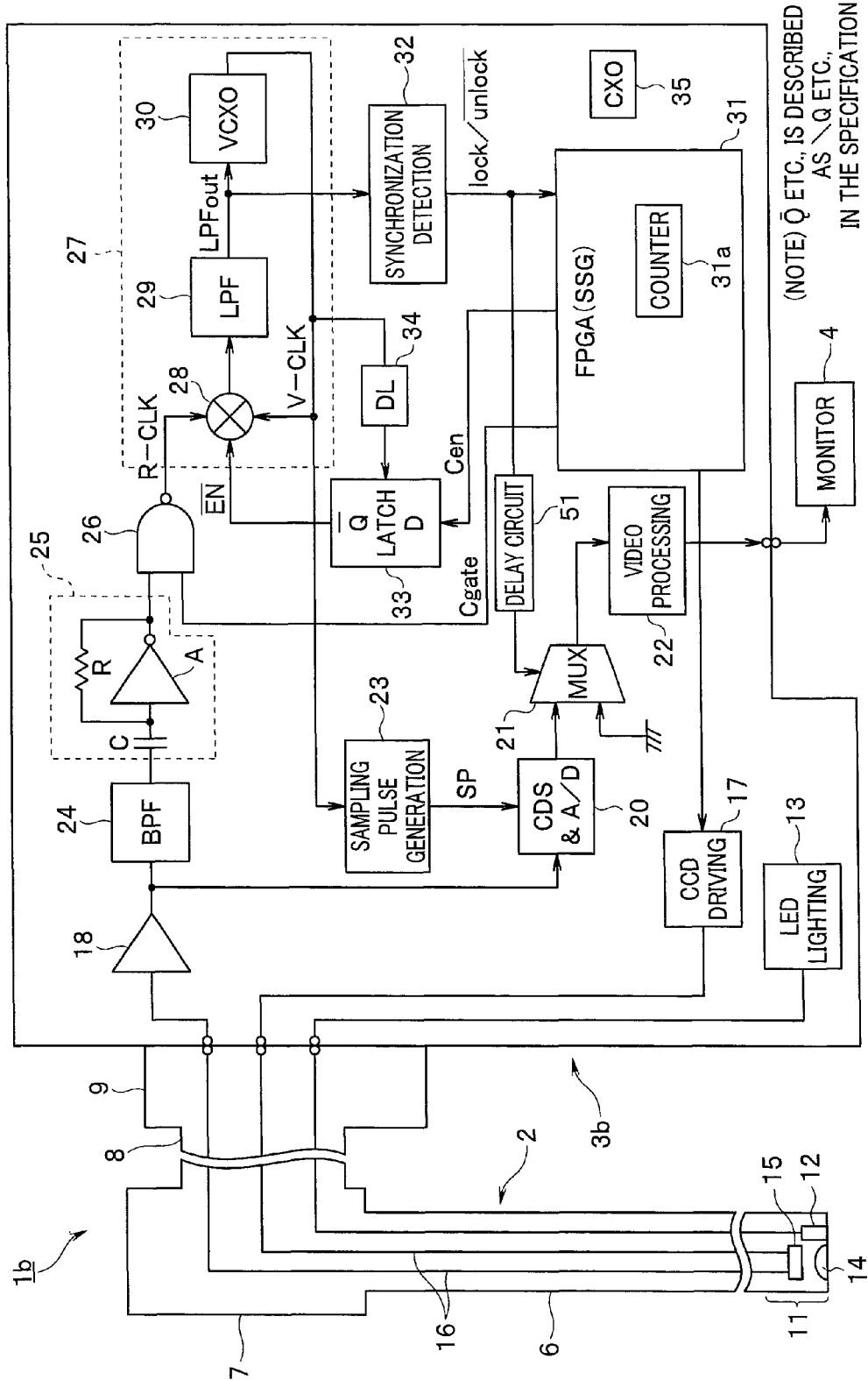
FIG. 4 illustrates a configuration of an endoscope system according to a second embodiment.

FIG. 4 illustrates a configuration of an endoscope system according to the second embodiment. Note that, in FIG. 4, the same components as those in FIG. 1 are indicated by the same reference numerals and description thereof will be omitted.

An endoscope system 1b in FIG. 4 is configured by using a processor 3b, instead of the processor 3 in the endoscope system 1 in FIG. 1. The processor 3b is configured by adding a delay circuit 51 to the processor 3 in FIG. 1.

The delay circuit 51 is provided between the synchronization detection circuit 32 and the multiplexer 21, and receives a detection signal (lock signal or \unlock signal) from the synchronization detection circuit 32. The delay circuit 51 delays the detection signal from the synchronization detection circuit 32 by a predetermined time period, and outputs a delay detection signal (delay lock signal or delay \unlock signal) to the multiplexer 21.

The multiplexer 21 selects the output from the CDS & A/D circuit 20 or the output of the dummy data (dummy signal) on the basis of the delay detection signal from the delay circuit 51, to output the selected one to the video processing circuit 22. Specifically, when receiving the delay lock signal as the delay detection signal, the multiplexer 21 selects the output from the CDS & A/D circuit 20 and outputs the signal from the CDS & A/D circuit 20 to the video processing circuit 22. On the other hand, when receiving the delay \unlock signal as the delay detection signal, the multiplexer 21 selects the dummy data and outputs the dummy data to the video processing circuit 22.

Next, the operation of the endoscope system 1b thus configured will be described.

FIG. 5 is a timing chart for describing the operation of the endoscope system 1b according to the second embodiment.

The synchronization detection circuit 32 outputs the \unlock signal of "L" level as the detection signal in the unstable period (unlock) during which the phase of the image pickup signal and the phase of the reference clock signal (variable clock) V-CLK are not synchronized with each other. Then, when the stable period (lock) during which the phase of the image pickup signal and the phase of the reference clock signal are synchronized with each other starts at the time T1, the synchronization detection circuit 32 outputs the lock signal of "H" level as the detection signal.

The detection signal from the synchronization detection circuit 32 is supplied to the delay circuit 51 and delayed by a predetermined time period T2. The delay detection signal (delay lock signal or delay \unlock signal) obtained by being delayed by the predetermined time period T2 by the delay circuit 51 is supplied to the multiplexer 21. According to such a configuration, the delay detection signal is switched from the delay \unlock signal of "L" level to the delay lock signal of "H" level at the time T1+T2.

When the delay \unlock signal of "L" level is inputted, the multiplexer 21 selects the dummy data and outputs the dummy data to the video processing circuit 22, and when the delay lock signal of "H" level is inputted, the multiplexer 21 selects the image pickup signal from the CDS & A/D circuit 20 and outputs the image pickup signal to the video processing circuit 22. Accordingly, until the time T1+T2, the fixed pattern such as black image is outputted to the monitor 4 from the video processing circuit 22, and after the time T1+T2, the endoscopic image obtained by performing video processing on the image pickup signal is outputted to the monitor 4 from the video processing circuit 22.

According to the endoscope system 1 in the first embodiment, immediately after the PLL circuit 27 is brought into the phase-synchronized state or in the frequency pull-in state (lock), switching from the fixed pattern to the endoscopic image is performed, whereby the endoscopic image is outputted. In this case, in a state where an image for one screen cannot be obtained in the phase-synchronized state or the frequency pull-in state, if the state of the PLL circuit 27 is returned from the phase-synchronized state or the frequency pull-in state (lock) to the non-pull-in state (\unlock) i.e., the state of phase-synchronization failure, there is a possibility that an endoscopic image in which a part of image is missing is displayed on the monitor 4.

In contrast, according to the endoscope system 1b of the present embodiment, the detection signal (lock signal or \unlock signal) from the synchronization detection circuit 32 is delayed by the predetermined time period T2 in the delay circuit 51 and inputted to the multiplexer 21. According to such a configuration, the endoscope system 1b is capable of outputting the endoscopic image with the phase-synchronized state or the frequency pull-in state (lock) being more stabilized.

The present invention is not limited to the above embodiments and modified example but various modifications thereof are possible without departing from the gist of the invention.

What is claimed is:

1. An endoscope system comprising:
   an endoscope comprising an image pickup device configured to pick up an image of a subject and to generate an image pickup signal based on the picked up image of the subject;
   a processor comprising:
      a signal processing circuit configured to perform signal processing on the image pickup signal;
      a voltage-controlled oscillator configured to generate a reference clock signal as a reference of a sampling pulse for sampling the image pickup signal;
      a phase-locked loop circuit configured to synchronize a phase of the image pickup signal with a phase of the reference clock signal;
      a pull-in detection circuit configured to:
         detect whether the phase of the image pickup signal and the phase of the reference clock signal are synchronized with each other by the phase-locked loop circuit,
         output a lock signal when it is detected that the phase of the image pickup signal and the phase of the reference clock signal are synchronized with each other, and
         output an unlock signal when it is detected that the phase of the image pickup signal and the phase of the reference clock signal are not synchronized with each other; and
      a multiplexer configured to:
         control the signal processing circuit to output a predetermined video in response to the unlock signal when it is detected that the phase of the image pickup signal and the phase of the reference clock signal are not synchronized with each other, and
         control the signal processing circuit to output a video signal obtained by processing the image pickup signal by the signal processing circuit in response to the lock signal when it is detected that the phase of the image pickup signal and the phase of the reference clock signal are synchronized with each other; and
   a delay circuit configured to delay the lock signal outputted from the pull-in detection circuit and indicating that the phase of the image pickup signal and the phase of the reference clock signal are synchronized with each other, by a predetermined time period, and to output the delayed lock signal to the multiplexer,
   wherein the multiplexer implements a switching section configured to switch between:

non-input of the image pickup signal to the signal processing circuit in response to the unlock signal, and
input of the image pickup signal to the signal processing circuit in response to the delayed lock signal, and
wherein the switching section is configured to output:
a dummy signal to the signal processing circuit in response to the unlock signal, and
the image pickup signal to the signal processing circuit in response to the delayed lock signal.

* * * * *